United States Patent
Okamoto et al.

(10) Patent No.: US 8,957,258 B2
(45) Date of Patent: Feb. 17, 2015

(54) BIS(1,1-DICHLORO-3,3,3-TRIFLUOROPROPYL) ETHER AND PROCESS FOR PREPARING THE SAME

(71) Applicant: Kanto Denka Kogyo Co., Ltd., Tokyo (JP)

(72) Inventors: Toshiaki Okamoto, Okayama (JP); Chizuko Okazaki, Okayama (JP)

(73) Assignee: Kanto Denka Kogyo Co., Ltd., Tokyo (JP)

( * ) Notice: Subject to any disclaimer, the term of this patent is extended or adjusted under 35 U.S.C. 154(b) by 0 days.

(21) Appl. No.: 14/357,861

(22) PCT Filed: Jan. 21, 2013

(86) PCT No.: PCT/JP2013/051057
§ 371 (c)(1),
(2) Date: May 13, 2014

(87) PCT Pub. No.: WO2013/111695
PCT Pub. Date: Aug. 1, 2013

(65) Prior Publication Data
US 2014/0336419 A1 Nov. 13, 2014

(30) Foreign Application Priority Data
Jan. 24, 2012 (JP) ................. 2012-011936

(51) Int. Cl.
*C07C 43/12* (2006.01)
*C07C 41/22* (2006.01)

(52) U.S. Cl.
CPC ............ *C07C 43/123* (2013.01); *C07C 41/22* (2013.01)
USPC .......................................... 568/684

(58) Field of Classification Search
None
See application file for complete search history.

(56) References Cited

U.S. PATENT DOCUMENTS

| 4,748,291 A | 5/1988 | Debras et al. |
| 2005/0049310 A1 | 3/2005 | Mjalli et al. |

FOREIGN PATENT DOCUMENTS

| JP | 62-230886 | 10/1987 |
| JP | 2000-351751 | 12/2000 |
| JP | 2007-501844 | 2/2007 |

OTHER PUBLICATIONS

John A. Young et al., "The Preparation of Some Derivatives of Chlorofluoroacetic Acid", Journal of the American Chemical Society, vol. 71, Jul. 1949, pp. 2432-2433.
John A. Young et al., "New Method of Preparation of Esters of Difluoroacetic Acid", Journal of the American Chemical Society, vol. 72, Apr. 1950, pp. 1860-1861.
Wojciech Dmowski et al., "Reactions of Sulfur Tetrafluoride With Carboxylic Acids", Polish Journal of Chemistry, 52, 71, 1978, pp. 71-85.
International Search Report, PCT/JP2013/051057, Apr. 16, 2013.
Edited by the Chemical Society of Japan, 4th edition Jikken Kagaku Koza 21, published by Maruzen Co., Ltd 1990, Nen, pp. 179 to 181.

*Primary Examiner* — Brian J Davis
(74) *Attorney, Agent, or Firm* — Young & Thompson

(57) ABSTRACT

The present invention provides a symmetrical ether compound which is chlorinated in the α position and which is useful as an intermediate for medicine and pesticides and as a raw material or a synthetic intermediate for producing a fluorine-containing compound, in particular a bis(1,1-dichloro-3,3,3-trifluoropropyl)ether represented by formula [1] which is obtained by chlorinating a bis(3,3,3-trifluoropropyl)ether. This bis(1,1-dichloro-3,3,3-trifluoropropyl)ether is produced by chlorinating, preferably under ultraviolet light irradiation, a bis(3,3,3-trifluoropropyl)ether [1].

2 Claims, No Drawings

BIS(1,1-DICHLORO-3,3,3-TRIFLUOROPROPYL) ETHER AND PROCESS FOR PREPARING THE SAME

TECHNICAL FIELD

This invention relates to bis(1,1-dichloro-3,3,3-trifluoropropyl) ether and a process for preparing the same.

BACKGROUND ART

Non-patent documents 1 to 3 below disclose an ether compound having a 1,1,3,3,3-pentafluoropropyl group which is analogous to the ether compound of the invention. However, these documents have no mention of a symmetrical ether compound having its α-positions chlorinated like the ether compound of the invention.

LIST OF CITATION

Non-Patent Document

Non-patent document 1: *Journal of the American Chemical Society* 71, 2432 (1949)
Non-patent document 2: *Journal of the American Chemical Society* 72, 1860 (1950)
Non-patent document 3: *Polish Journal of Chemistry* 52(1), 71-85 (1978)

SUMMARY OF THE INVENTION

Problem to be Solved by the Invention

An object of the present invention is to provide a symmetrical ether compound having the α-positions chlorinated that is useful as an intermediate of pharmaceuticals and agricultural chemicals or a starting material or an intermediate for synthesizing fluorine-containing compounds.

Means for Solving the Problem

The inventor has conducted extensive study to solve the above problem and as a result succeeded in synthesizing a novel symmetrical ether compound having the α-positions chlorinated and found that the ether compound accomplishes the above object of the invention. The invention has been completed based on this finding.

The invention provides bis(1,1-dichloro-3,3,3-trifluoropropyl) ether represented by formula (1):

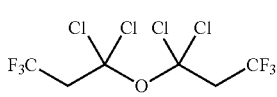

[1]

The invention also provides a process for preparing bis(1,1-dichloro-3,3,3-trifluoropropyl) ether represented by formula (1). The process comprises chlorinating bis(3,3,3-trifluoropopyl) ether represented by formula (2):

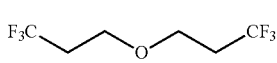

[2]

Effect of the Invention

Bis(1,1-dichloro-3,3,3-trifluoropropyl) ether of the invention is an extremely important compound as an intermediate for pharmaceuticals and agricultural chemicals or a starting material for synthesizing fluorine-containing compounds having a trifluoromethyl group at the terminal.

BEST MODE FOR CARRYING OUT THE INVENTION

Bis(1,1-dichloro-3,3,3-trifluoropropyl) ether and a preferred embodiment of a process for preparing the same according to the invention will be described. It should be noted, however, that the invention is not deemed to be limited thereto, and various changes and modifications can be made therein without departing from the spirit and scope thereof.

[1] Structure

Bis(1,1-dichloro-3,3,3-trifluoropropyl) ether of the invention is a symmetrical ether compound having the α-positions thereof chlorinated, being represented by formula (1).

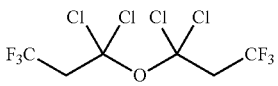

[1]

[2] Properties

The ether compound of the invention is a colorless transparent liquid compound and stable per se.

[3] Use

It is possible that the ether compound of the invention have its α-positions converted to carbonyl by hydrolysis. the ether compound is easier to handle than heretofore reported intermediates for fluorine-containing compounds or fluorinating agents because of its high stability and resultant low risk. The carbonyl compound obtained by hydrolysis is useful as a starting material or intermediate for pharmaceuticals and agricultural chemicals. Understandably, the ether compound of the invention is also useful as an intermediate for the syntheses.

[4] Process for Preparation

Bis(1,1-dichloro-3,3,3-trifluoropropyl) ether of the invention is obtained by chlorinating the α-positions of bis(3,3,3-trifluoropropyl) ether represented by formula (2), which is synthesized by a known process, as shown in reaction scheme 1 below.

The known process for synthesizing bis(3,3,3-trifluoropropyl) ether of formula (2) is exemplified by the process described in *Journal of Organic Chemistry* 28, 492 (1963).

Reaction scheme 1

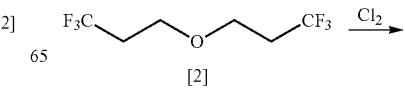

[2]

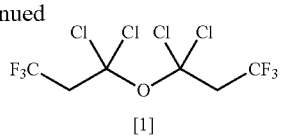

The manner of chlorination reaction is not particularly limited. For example, the chlorination reaction can be carried out by causing chlorine to react on bis(3,3,3-trifluoropropyl) ether in a liquid or gas phase using a radical initiator or under UV irradiation. The process comprising causing chlorine to react under UV irradiation is preferred.

That is, bis(1,1-dichloro-3,3,3-trifluoropropyl) ether of the invention is prepared by causing chlorine to react on bis(3,3,3-trifluoropropyl) ether under UV irradiation.

Preparation of bis(1,1-dichloro-3,3,3-trifluoropropyl) ether of the invention will be described in detail with reference to the process comprising causing chlorine to react on bis(3,3,3-trifluoropropyl) ether under UV irradiation.

Chlorine that can be used in the invention preferably has a concentration of 10% to 100%, more preferably 90% to 100%. Chlorine is used in an amount preferably of 4 to 10 mols, more preferably 4 to 5 mols, per mole of the reaction substrate.

The reaction temperature is preferably −20° to 50° C., more preferably 0° to 20° C. At 70° C. or higher temperatures, is unfavorable because bis(1,1-dichloro-3,3,3-trifluoropropyl) ether decomposes by the action of by-produced (by product) hydrogen chloride.

In order to increase the chlorination efficiency, it is preferred that the substrate and chlorine be allowed to react with each other in a liquid phase under UV irradiation. The reactor to be used may be, for example, a glass vessel equipped with a light source. While the reaction proceeds even under UV light from outside the reactor, it is preferred to use a light source inserted inside the reactor from the viewpoint of light use efficiency. Example of suitable light sources are a high, ultrahigh, or low pressure mercury lamp and a UV LED.

The wavelength of the UV rays for use in the reaction is preferably 312 to 577 nm, more preferably 312 to 493 nm.

The reaction does not need a reaction solvent but can carried out in a solvent inert to the reaction. Examples of useful solvents are water, carbon tetrachloride, dichloromethane, and mixtures thereof.

As the reaction proceeds, the hydrogen chloride is by-produced (by product). It is advisable that the generated hydrogen chloride be released from the reaction system and absorbed by water, an aqueous alkali solution, or the like.

After completion of the reaction, chlorine remaining in the reaction mixture is expelled by bubbling with nitrogen. The by-produced (by product) hydrogen chloride is then removed by the addition of an aqueous basic solution, such as a potassium hydroxide aqueous solution. Subsequently, a sodium sulfite aqueous solution is added to reduce any residual chlorine. The lower liquid phase is collected to yield a desired product, which is purified by distillation.

In the case when the chlorination reaction is carried out using a radical initiator, the reaction can be performed according to a conventional manner for chlorination using a radical initiator. After the reaction, the reaction mixture is worked up in the same manner as described with respect to the chlorination reaction under UV irradiation.

Examples of the radical initiator include azobisisobutyronitrile and benzoyl peroxide.

EXAMPLES

The invention will now be illustrated in greater detail with reference to Example, but the invention is not construed as being limited thereto.

Example 1

Synthesis of bis(1,1-dichloro-3,3,3-trifluoropropyl) ether

In a glass-made 200 ml-photoreactor equipped with a stirrer, a thermometer, a 100 W high pressure mercury lamp, a Dimroth condenser, and a chlorine gas inlet tube were put 210 g (1.00 mol) of bis(3,3,3-trifluoropropyl) ether and cooled in an ice/water bath. The high pressure mercury lamp (UVL100HA from Riko Kagaku Sangyo K.K.) was turned on to irradiate the reaction mixture with UV light of 312 to 577 nm. Into the reaction system was introduced 5.10 mol of chlorine at a rate of 480 ml/min over 5 hours while stirring the mixture using a magnetic stirrer. The chlorination reaction temperature reached 20° to 30° C. as a result of reaction heat. After completion of the reaction, the reaction mixture was analyzed by gas chromatography. The starting material, bis(3,3,3-trifluoropropyl) ether, was not detected. The gas chromatographic area percent of bis(1,1-dichloro-3,3,3-trifluoropropyl) ether was found to be 83.0%.

Nitrogen was made to flow through the reaction mixture, and water was added thereto. Residual chlorine was removed by reduction using a 10% sodium sulfite aqueous solution and a 48% potassium hydroxide aqueous solution while stirring in an ice/water bath, followed by liquid-liquid separation to collect a desired product, which was dried over sodium sulfate. Following the removal of the desiccant by filtration, the ether solution was distilled under reduced pressure to collect a fraction having a boiling point of 70° to 71° C. (1 kPa) to give 230.75 g of bis(1,1-dichloro-3,3,3-trifluoropropyl) ether in a yield of 65%. The gas chromatographic area percent of the fraction was 98.1%. The spectral data of the resulting bis(1,1-dichloro-3,3,3-trifluoropropyl) ether are shown below.

1H-NMR spectrum (500 MHz, CDCl$_3$) δ (ppm): 3.39 (4H, q, J=9.0 Hz)

19F-NMR spectrum (470 MHz, CDCl$_3$) δ (ppm): −62.0 (6F, t, J=9.0 Hz)

MS spectrum (m/z): 165 (CF$_3$CH$_2$CCl$_2$), 111 (CF$_3$CH$_2$CO), 83 (CF$_3$CH$_2$), 69 (CF$_3$).

The invention claimed is:

1. Bis(1,1-dichloro-3,3,3-trifluoropropyl) ether represented by formula (1):

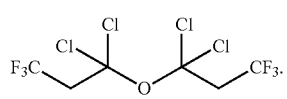

2. A process for preparing bis(1,1-dichloro-3,3,3-trifluoropropyl) ether comprising chlorinating bis(3,3,3-trifluoropropyl) ether represented by formula (2):

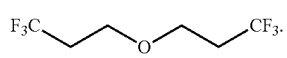

* * * * *